United States Patent [19]

Kawamata

[11] Patent Number: 5,727,259
[45] Date of Patent: Mar. 17, 1998

[54] ONE-TOUCH TENSION ADJUSTMENT DEVICE FOR GOGGLE

[75] Inventor: Kenji Kawamata, Matsudo, Japan

[73] Assignee: Kawamata Koki Mfg. Co., Ltd., Matsudo, Japan

[21] Appl. No.: 814,659

[22] Filed: Mar. 11, 1997

[30] Foreign Application Priority Data

| Apr. 18, 1996 | [JP] | Japan | 8-132509 |
| Aug. 13, 1996 | [JP] | Japan | 8-245394 |

[51] Int. Cl.⁶ .................................................. A61F 9/02
[52] U.S. Cl. ............................................................ 2/452
[58] Field of Search ............................ 2/452, 428, 430, 2/426, 421; 24/614, 615, 585

[56] References Cited

U.S. PATENT DOCUMENTS

| 4,527,292 | 7/1985 | Kasama et al. | 2/452 |
| 4,564,960 | 1/1986 | Nishiyama | 2/452 |
| 4,712,280 | 12/1987 | Fildan | 24/633 X |
| 4,727,630 | 3/1988 | Alan | 24/633 X |
| 5,181,280 | 1/1993 | Zachry | 2/452 |
| 5,303,428 | 4/1994 | Pernicka | 2/452 |
| 5,406,340 | 4/1995 | Hoff | 2/452 X |
| 5,410,763 | 5/1995 | Bolle | 2/452 X |
| 5,524,300 | 6/1996 | Chiang | 2/452 X |
| 5,611,644 | 3/1997 | Lutz | 24/585 X |
| 5,642,178 | 6/1997 | Leonardi et al. | 2/452 X |
| 5,657,493 | 8/1997 | Ferrero et al. | 2/452 X |

FOREIGN PATENT DOCUMENTS

| 2477410 | 9/1981 | France | 2/452 |

*Primary Examiner*—C. D. Crowder
*Assistant Examiner*—Shirra L. Jenkins
*Attorney, Agent, or Firm*—Kanesaka & Takeuchi

[57] ABSTRACT

A one touch tension adjustment device for a goggle attachment holes. Each end of an expandable strap is passed through the attachment holes in the goggles and through a tension adjustment stopper and finally to a connection means. This arrangement creates an overlapping area of the strap. A sliding area for allowing the tension of the goggles to be controlled is also created. When the connection device is released, the tension adjustment stoppers slide toward the attachment holes of the goggles along the sliding area until the tension adjustment stoppers abut the attachment holes and thus allow the tension of the strap to be reduced without causing the goggles to become dislodged from the face of the wearer.

7 Claims, 9 Drawing Sheets

ONE-TOUCH TENSION ADJUSTMENT DEVICE FOR GOGGLE

BACKGROUND OF THE INVENTION AND RELATED ART STATEMENT

This invention relates to a one-touch tension adjustment device for a goggle.

Underwater or swimming goggles are widely used in recreational as well as competitive swimming. Recently, in particular, swimming goggles with lenses for correcting eyesight have frequently been used by people who need eyeglasses to correct nearsight, farsight, and astigmatism (hereafter referred to as eyeglass users). However, since there has been no device which allows one-touch tension adjustment for a rubber strap of a swimming goggle, eyeglass users can not use the swimming goggle for other purposes. Namely, the swimming goggle has to change to regular eyeglasses to avoid uncomfortable feeling by pressure on their eye region and face outside the water. Consequently, although eyeglass users know about the swimming goggles with lenses for correcting eyesight (hereafter referred to as prescription goggles), these goggles can not be fully utilized, and eyeglass users have to be excessively careful to avoid problems and dangers associated with poor eyesight.

Because the swimming goggle has so far been designed for underwater use only, when the eyeglass user wears prescription goggle, because of the uncomfortable pressure outside water, the user has to slide the goggle up onto the forehead or down around the neck, or take them off, and is forced to experience the inconvenience of always carrying regular eyeglass separately.

Thus, the purpose of this invention is to avoid inconvenience of the conventional goggle, and to provide a goggle with a strap adjustment so that the goggle can be used both inside and outside water by eliminating the uncomfortable pressure outside water for eyeglass user, who now needs only a prescription goggle without annoyance of changing to eyeglasses and can avoid the danger and trouble associated with poor eyesight.

SUMMARY OF THE INVENTION

In a first aspect of the invention, one touch tension adjustment device for a goggle of the invention is formed of an expandable strap attached to the goggle and having first and second end portions, the first end portion having a sliding area; a connecting device attached to an end of the first end portion to fix the end of the first end portion to the strap other than the first end portion to increase an overlapping area of the strap in a tension apply condition for the strap, and a tension adjustment stopper fixed to the strap at an end of the sliding area near the connecting device. In the tension apply condition for the strap, when the connecting device is released, the overlapping area of the strap is reduced to reduce tension of the tension apply condition, and the tension adjustment stopper moves close to the goggle.

In a second aspect of the invention, one touch tension adjustment device for a goggle is formed of a first expandable strap attached to one side of the goggle at one end thereof; an insert connected to the other end of the first strap, and having teeth on one surface thereof; a second expandable strap attached to the other side of the goggle at one end thereof; and a socket connected to the other end of the second strap. The socket includes a hole for allowing the first strap to pass therethrough, a holding flap to engage the teeth of the insert, and a releasing device attached to the holding flap to move the flap in a direction away from the teeth to thereby permit the teeth of the insert from disengaging from the holding flap.

The one touch tension adjustment device for a goggle of the invention has the features of easy installation and a tension adjustment function. Due to the tension adjustment function outside water, tension of rubber straps can be reduced to the extent that the goggle does not slide down, but stay in the proper position to provide to a wearer a feeling similar to that of regular eyeglasses, and in water, the tension of the rubber straps can be increased by a one-touch operation, so that the goggle is fixed in position with watertight even while the wearer is in active motion.

DETAILED DESCRIPTION OF PREFERRED EMBODIMENTS

Figure 1:
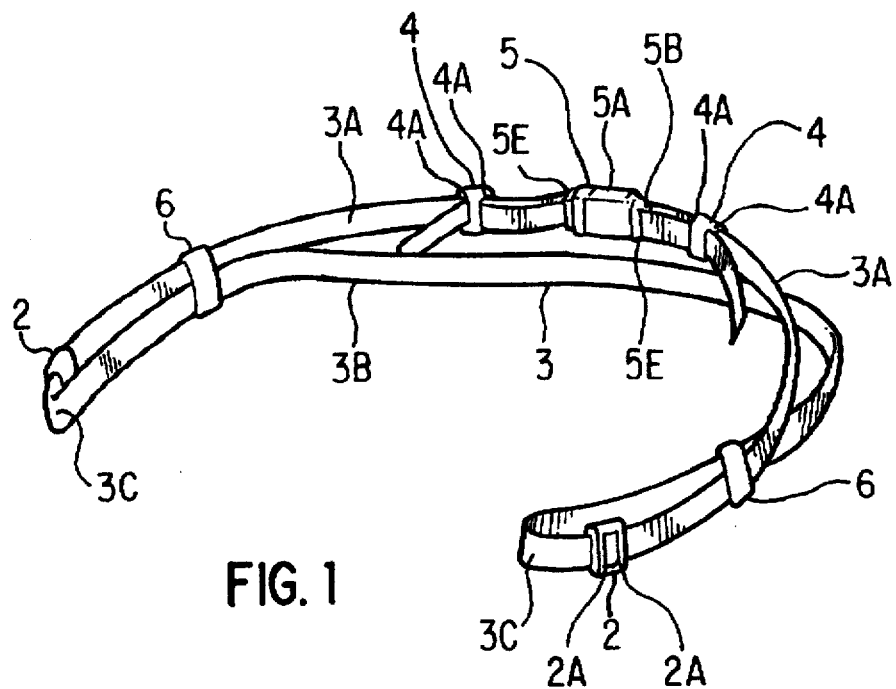
FIG. 1 is a perspective view of a double-layer type one-touch strap of a first embodiment of the invention.

FIG. 1 is a perspective view of a double-layer type one-touch strap. The one-touch strap is formed of a single rubber strap 3 which is attached to a main body of a goggle through strap attachment holes 1A, and folded at rubber strap folding area 3C into double layers. The one-touch strap has two functionally different sections, which are two end portions or connection-disconnection sections 3A, and a holding section 3B. The holding section 3B wraps around and presses a user's head for holding the goggle in the proper position with an appropriate tension all the time, and the connection-disconnection sections 3A have the function of adjusting the tension of the holding section 3B.

Figure 11:
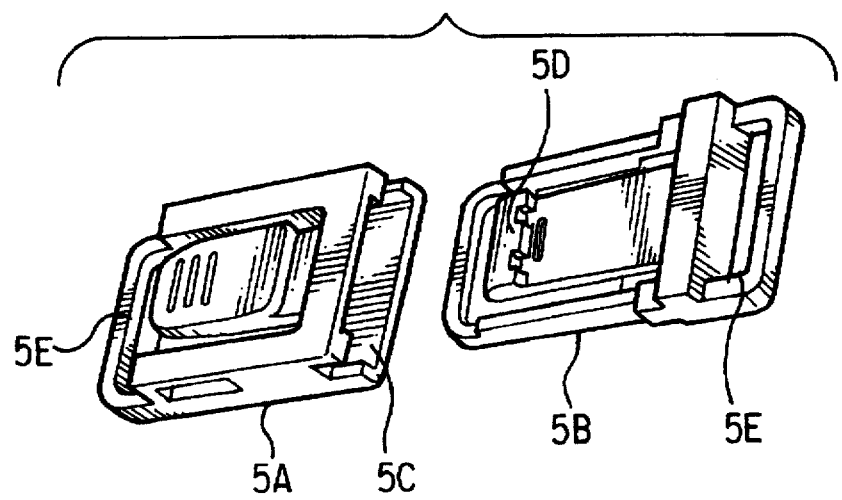
FIG. 11 is a perspective view of a strap clasp used in the invention.
Figure 12A:
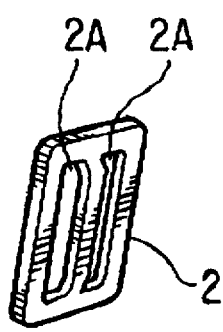
FIG. 12(a) is an enlarged perspective view of a tension-adjustment stopper.
Figure 12B:
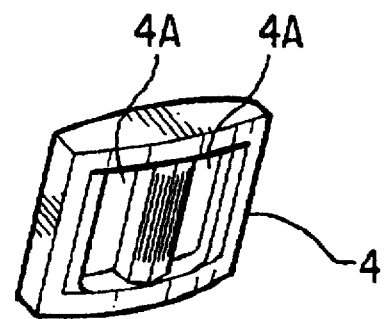
FIG. 12(b) is an enlarged perspective view of a length-adjustment piece.

Each of the connection-disconnection section 3A passing through the strap attachment hole 1A is arranged such that an end of the rubber strap 3 passes through openings 2A of a tension adjustment stopper 2 (FIG. 12(a)), openings 4A of a length-adjustment piece 4 (FIG. 12(b)), an opening 5E of a strap clasp 5 (FIG. 11), and then turns back to pass again through the openings 4A of the same length-adjustment piece 4.

As shown in FIG. 11, the strap clasp 5 is formed of two parts, i.e. strap clasp socket 5A and strap clasp insert 5B, which can be easily locked and released. When the strap clasp insert 5B is placed into an opening 5C of the strap clasp socket 5A, a hook 5D is engaged by a catch located inside the strap clasp socket 5A (not shown), and the socket 5A and the insert 5B are firmly snapped together. When the center portion of the socket 5A is pressed, the hook 5D is released, and the socket 5A and the insert 5B are easily separated.

The connection-disconnection sections 3A are connected by the strap clasp 5 to strongly press the goggle to the wearer, and are separated from each other to moderately press the goggle to the wearer.

When the strap clasp 5 is opened in a condition that the goggle is used, the connection-disconnection sections 3A come loose and, at a sliding area, slide through strap loops 6 toward the center of the rubber strap 3, to thereby release the tension of the holding section 3B. As a result, the goggle is supported solely by the weaker tension of the holding section 3B. The length of the holding section 3B is set to maintain appropriate tension by installing the tension adjustment stoppers 2 to prevent the goggle from slipping down or exerting uncomfortable pressure on a user's eye region and face. Namely, the length of the holding section 3B can be adjusted to maintain appropriate tension to prevent the goggle from slipping down and exerting uncomfortable pressure on the user's eye region and face by adjusting the location of the tension adjustment stoppers 2 on the strap 3.

Figure 2:
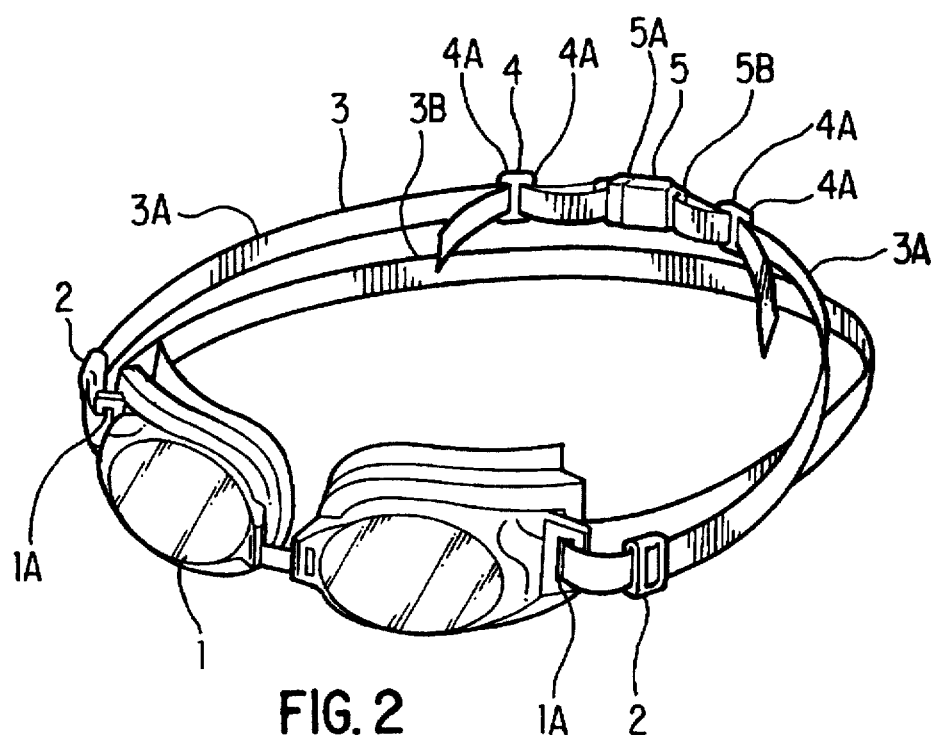
FIG. 2 is a perspective view of a double-layer type one-touch strap of the first embodiment of the invention directly attached to a main body of a swimming goggle.
Figure 12C:
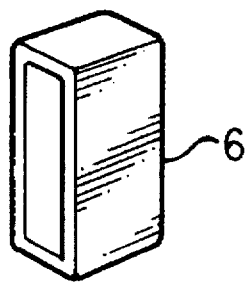
FIG. 12(c) is an enlarged perspective view of a strap loop.

The tension-adjustment stopper 2 which has right and left openings 2A (FIG. 12(a)) can slid along the rubber strap connection-disconnection section 3A with slight friction to be fixed at the desired position. When the strap clasp 5 is opened or released, the rubber strap 3 moves through the strap attachment hole 1A until the tension-adjustment stopper 2 abuts against the strap attachment hole 1A of the goggle (shown in FIG. 2). Therefore, the length of the holding section 3B is defined by the position of the tension-adjustment stopper 2. The strap loop 6, as shown in FIGS. 1 and 12(c), is set for the adjustment of the length of the hanging portion of the connection-disconnection section 3A when the clasp 5 is opened.

As described above, when the center portion of the strap clasp socket 5A is pressed, the strap clasp 5 opens and the tension of the rubber strap is reduced. Thus, uncomfortable pressure on a user's eye region and face is eliminated, and yet the tension of the rubber strap is adequately maintained to keep the goggle in a comfortable wearing position similar to that of the regular eyeglasses. With this device, eyeglass users can very effectively avoid the danger and problem associated with poor eyesight. When the released socket 5A and the insert 5B are engaged together, the goggle can be strongly pressed again to the wearer.

Figure 3:
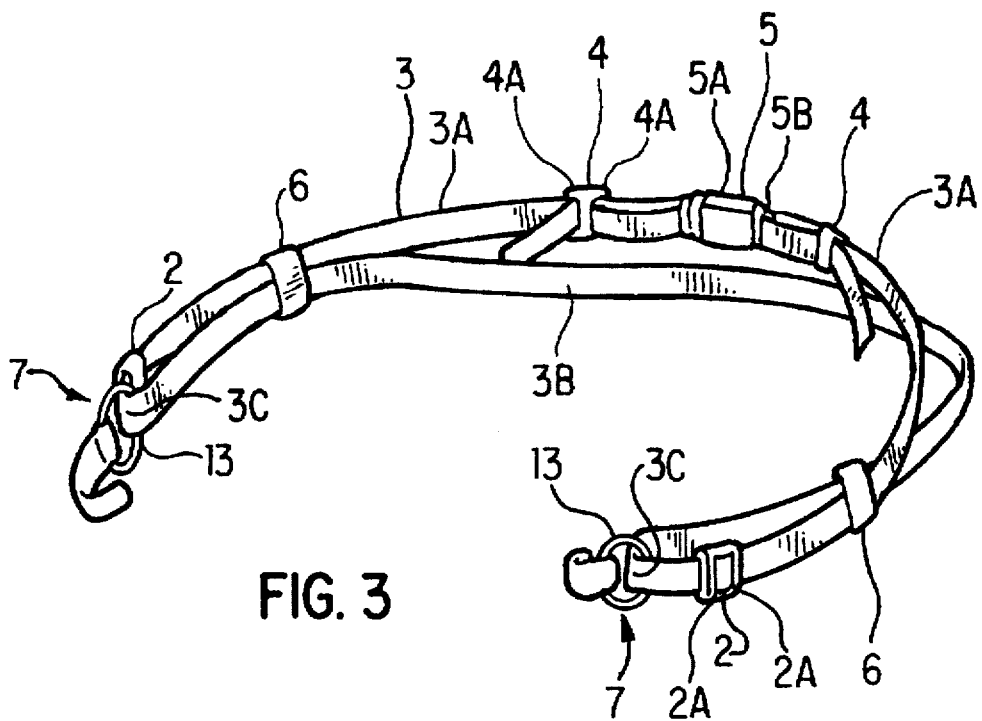
FIG. 3 is a perspective view of a double-layer type one-touch strap with a pair of strap attachment fixtures of the first embodiment of the invention.
Figure 4:
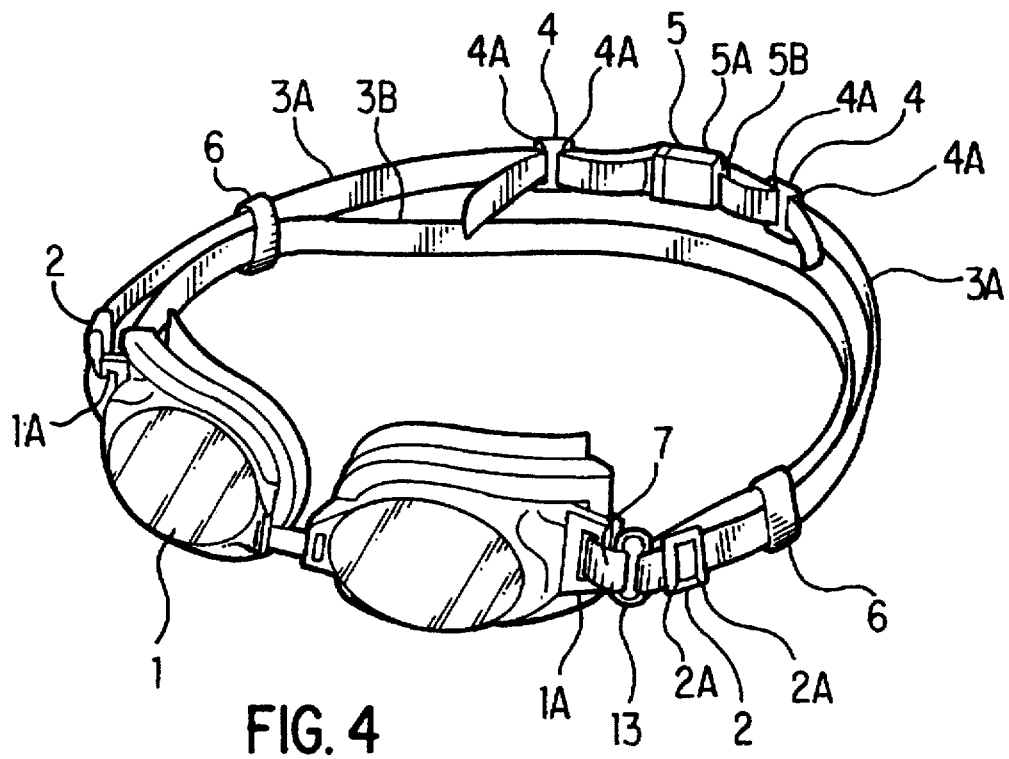
FIG. 4 is a perspective view of a double-layer type one-touch strap with a pair of strap attachment fixtures of the first embodiment of the invention attached to the swimming goggle.
Figure 12D:
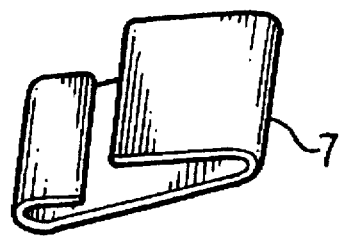
FIG. 12(d) is an enlarged perspective view of a strap attachment fixture.
Figure 12E:
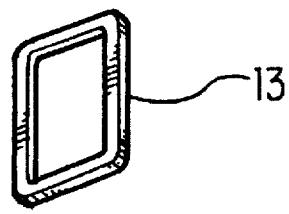
FIG. 12(e) is an enlarged perspective view of a rubber strap connection ring.

Depending on the situation, as shown in FIG. 3, the one-touch strap can be attached to the goggle at the strap attachment holes 1A with hooks of strap attachment fixtures 7 (FIG. 12(d)). Namely, the strap 3 is not directly attached to the goggle, but the strap 3 may have rubber strap connection rings 13 (FIG. 12(e)) at the areas 3C of the strap, which may be connected to the strap attachment fixtures 7 connected to the goggle. This method can be applied to all the embodiments of this invention.

In this embodiment, in order to reduce the number of parts, the invention may be modified. Namely, the rubber strap 3 may pass through the strap attachment holes 1A of the goggle's main body and folded at the areas 3C; the tension-adjustment stoppers 2 are installed at the proper positions of the right and left sides of the rubber strap connection-disconnection sections 3A; one end of the rubber strap 3 is fixed to one of the strap clasp parts 5A and 5B; and, the other end of the rubber strap 3 passes through the length-adjustment piece 4 and the other of the strap clasp parts 5A and 5B, and passes again the same length-adjustment piece 4. As a result, one length-adjustment piece 4 can be omitted. This embodiment uses a single rubber strap whose proper full length is, for example, about 100 to 130 cm.

Figure 5:
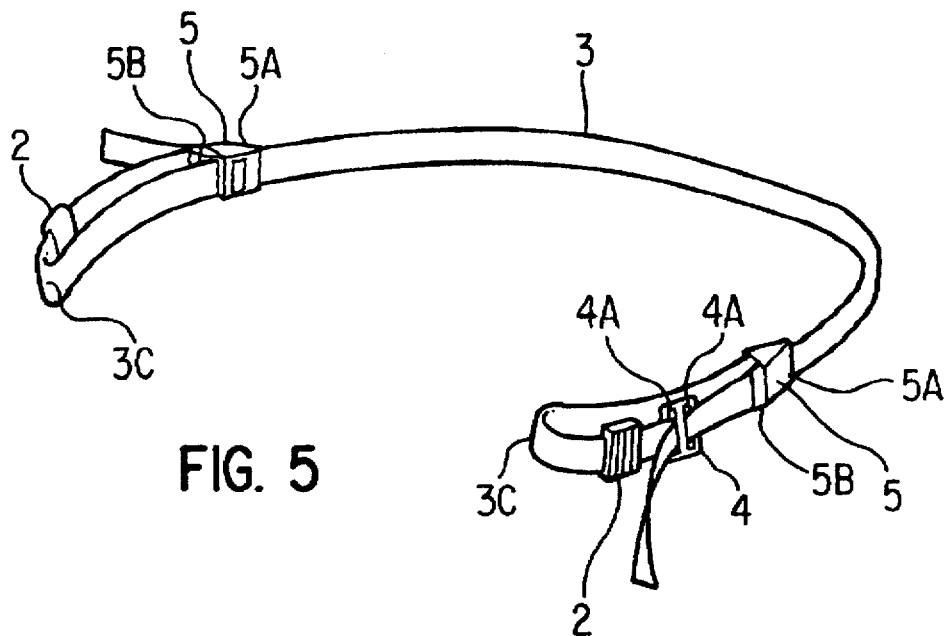
FIG. 5 is a perspective view of a single-layer type one-touch strap of a second embodiment of the invention.
Figure 6:
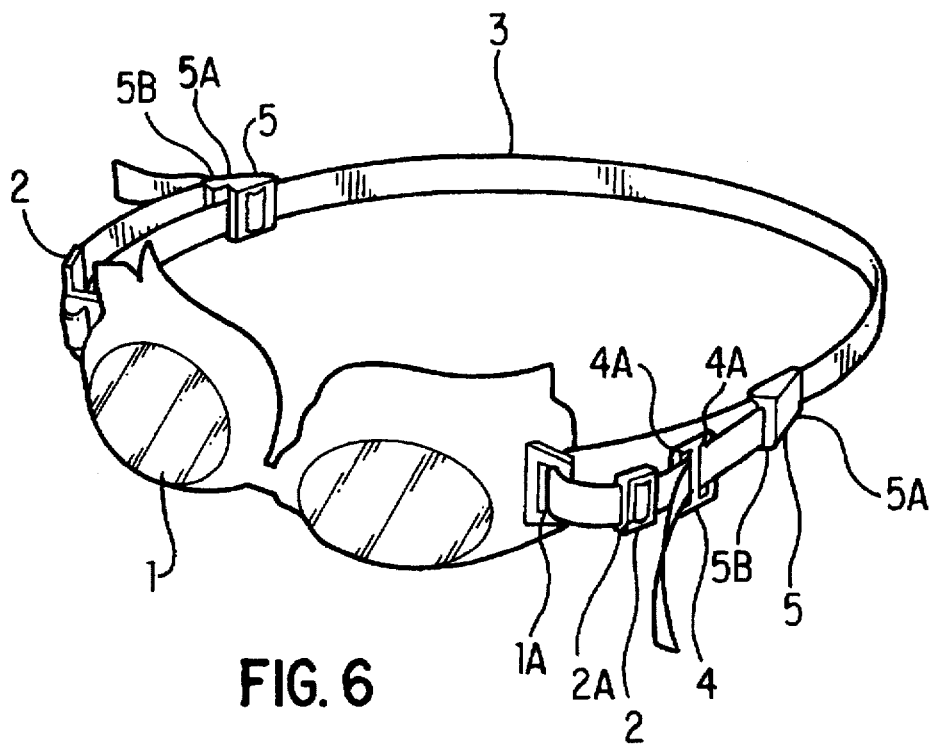
FIG. 6 is a perspective view of a single-layer type one-touch strap of the second embodiment of the invention directly attached to a main body of a swimming goggle.

FIG. 5 is a perspective view of a second embodiment of a single-layer type one-touch strap of the invention. FIG. 6 is a perspective view of the embodiment attached to a main body of a goggle.

Each end of a rubber strap 3 extends through a strap clasp socket 5A first and then a strap attachment hole 1A of a goggle, and is folded at the area 3C. The rubber strap 3 then passes through a tension adjustment stopper 2, a length-adjustment piece 4 and a strap clasp insert 5B. The rubber strap is folded at the strap clasp insert 5B, returns back to the same length-adjustment piece 4, and is tightened there.

This embodiment uses two strap clasps 5 at the right and left sides of the rubber strap, but it can be used in the same way as in the double-layer type example. The strap clasp 5 as well as all the other parts used in this embodiment are similar to those used in the first embodiment. In this embodiment, not only the same effect as in the first embodiment is assured by operating the right and left strap clasps 5 in the same way as in the first embodiment, but also the rubber strap structure can be simplified. This embodiment also uses a single rubber strap whose proper full length is, for example, about 70 to 90 cm.

Incidentally, the proper full lengths of the rubber straps are about 100 to 130 cm for the double-layer type in the first embodiment, and about 70 to 80 cm for the single-layer type in the second embodiment. The width of the rubber straps in both embodiments is about 8 to 15 mm for the strength of the rubber straps, stable fit and appearance. The openings of the tension adjustment stopper 2 in FIG. 12(a) should have a narrowest space, through which one rubber strap can pass, and the openings of the length-adjustment piece 4 in FIG. 12(b) should have a narrowest space through which two rubber straps can pass, because these limited spaces prevent loosening of the rubber straps. The strap clasp 5 in FIG. 11 is formed of two separate parts, i.e. strap clasp socket 5A and strap clasp insert 5B, and the two parts can be easily opened by pressing the central or bottom part of the socket 5A. The strap loop 6 in FIG. 12(c) has a space wide enough but not too wide for two rubber straps to pass through and prevents the rubber straps from hanging down when the strap clasp 5 is opened. These parts can be easily attached to any types of the goggles with different shapes and positions of strap attachment holes, and can also provide the goggles with effective functions.

Figure 8:
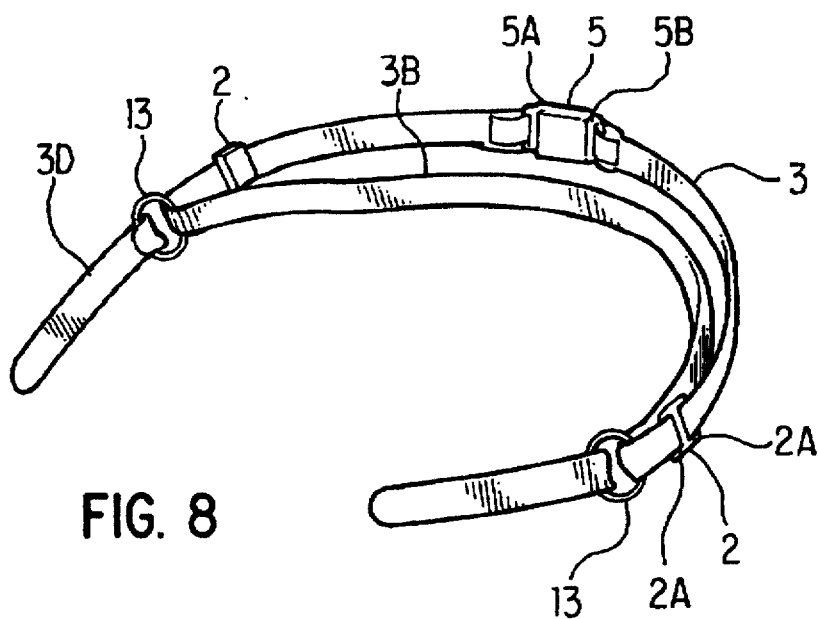
FIG. 8 is a perspective view of a double-layer type one-touch strap of the third embodiment of the invention attached to a swimming goggle.
Figure 7:
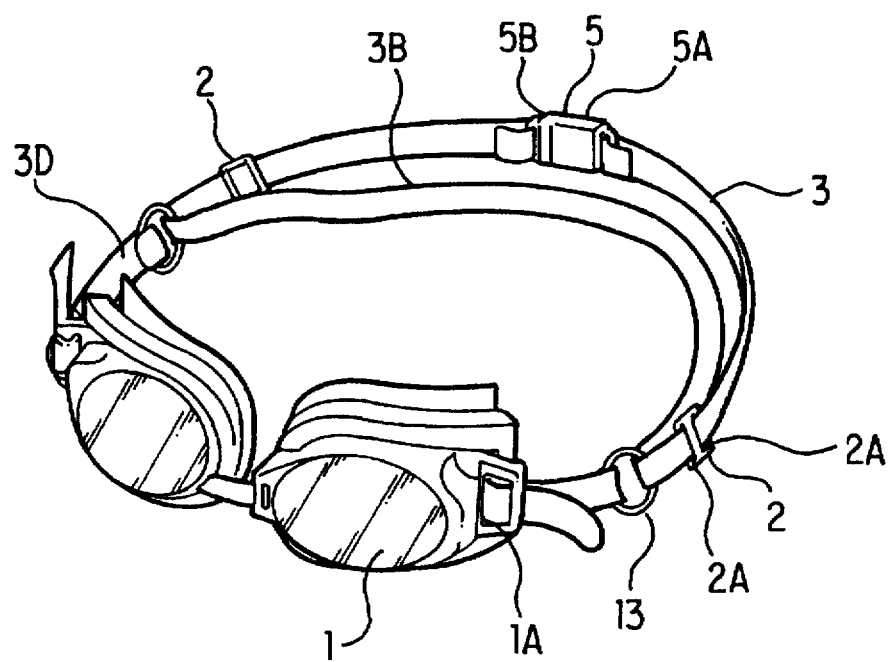
FIG. 7 is a perspective view of a double-layer type one-touch strap with a pair of single-layer length-adjustable straps of a third embodiment of the invention.

FIG. 7 is a perspective view of a double-layer type one-touch strap of a third embodiment of the invention. As shown in FIG. 8, a pair of rubber straps 3D has about 10 to 15 cm in length, and is attached to right and left strap attachment holes 1A of a main body of a goggle, respectively. Each strap 3D is fixed to a rubber strap connection ring 13.

Most goggle has a function at the strap attachment hole 1A to adjust the length of the rubber strap and to fix the rubber strap. For a goggle without this function, the same function can be obtained by inserting the rubber strap 3D into the attachment hole 1A, and after turning the rubber strap 3D, installing the length-adjustment piece 4 (see FIG. 12(b)).

A rubber strap holding section 3B, which is located behind the head is formed of a 50 to 60 cm long rubber strap. Each end of the rubber strap 3B passes through the rubber strap connection ring 13 and tension-adjustment stopper 2, and both ends of the rubber strap 3B are fixed to a socket 5A and an insert 5B of a strap clasp 5.

To adjust the goggle for use, first, each length of the rubber straps 3D is adjusted so that the tension is sufficient to prevent leakage of water into the goggle but is not so strong as to cause discomfort to the user's eye region and face. Next, the positions of the tension-adjustment stoppers 2 are selected to maintain the goggle in a proper position when the strap clasp 5 is opened and the tension is released. In this embodiment, results similar to those obtained in other embodiments can be obtained, and furthermore, there are some advantages, such as elimination of entanglement of the rubber straps, cost reduction due to a small number of parts, and simplified handling.

For the third embodiment, the rubber strap 3D has the length of 10 to 15 cm, the rubber strap 3B has the length of 50 to 60 cm, and their width is about 8 to 15 mm. The total length of the straps can be adjusted by the shorter rubber straps. The longer strap is folded in two with the proper length to fit around the back of the head.

Figure 9:
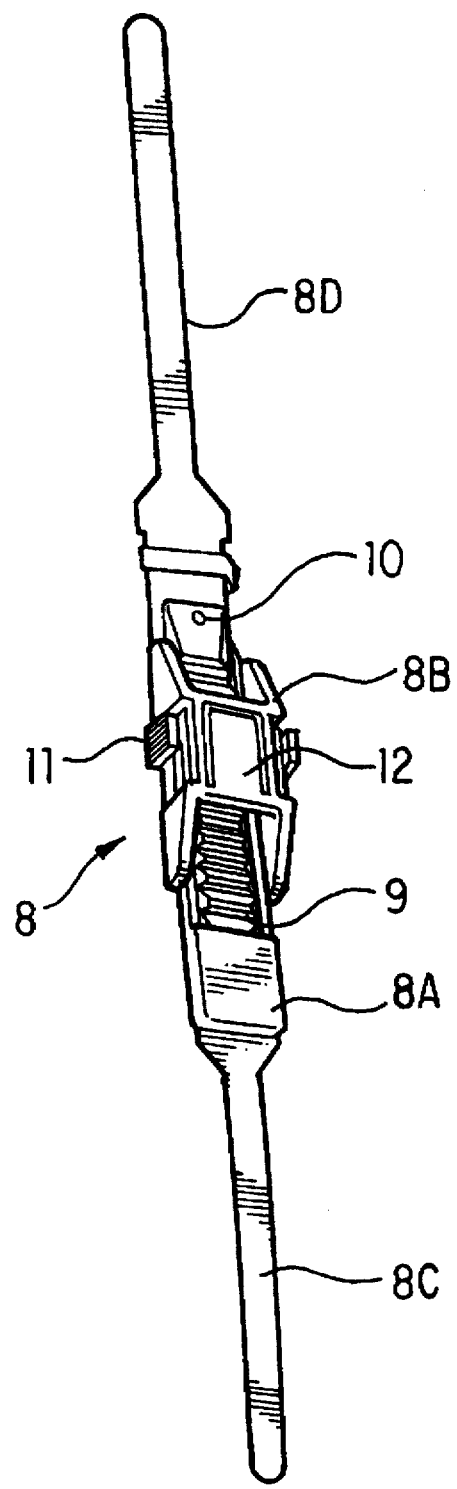
FIG. 9 is a perspective view of a slide-type one-touch strap clasp (slide stopper) with a pair of rubber straps of a fourth embodiment of the invention.
Figure 10:
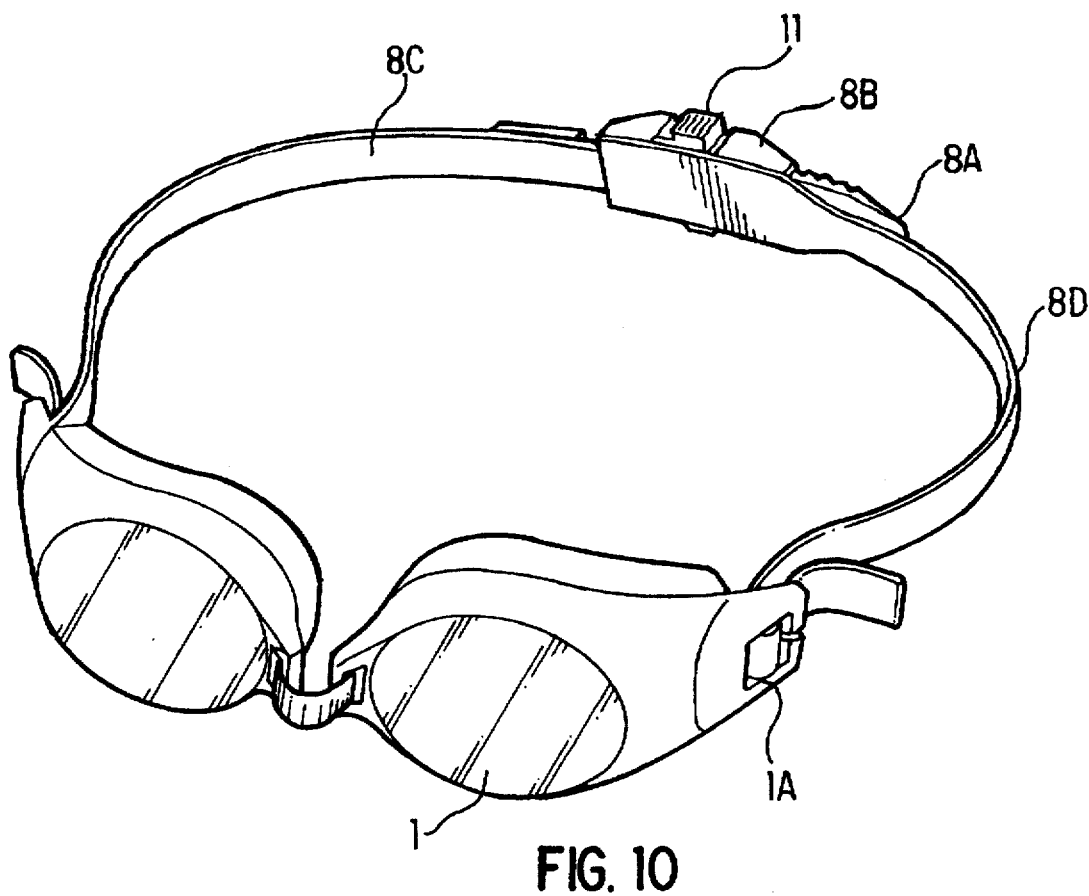
FIG. 10 is a perspective view of a slide-type one-touch strap of the fourth embodiment of the invention attached to a swimming goggle.
Figure 13A:
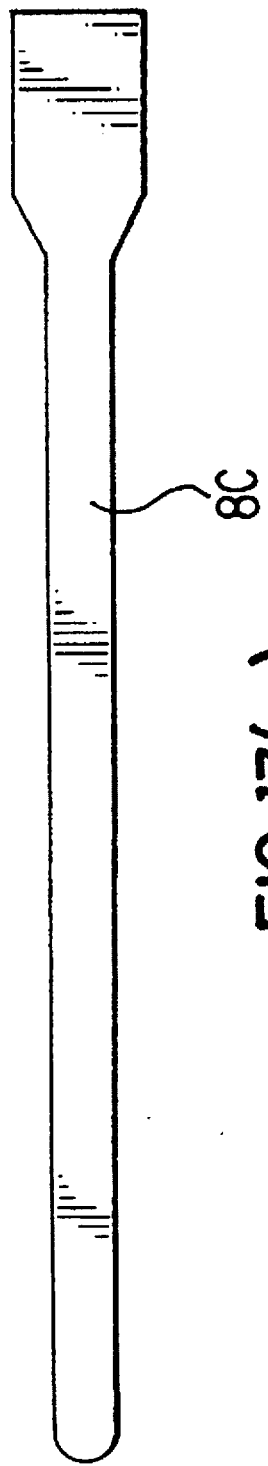
FIGS. 13(a) and 13(b) are plan views of a pair of rubber straps used in a slide-type one-touch strap of the invention.
Figure 13B:
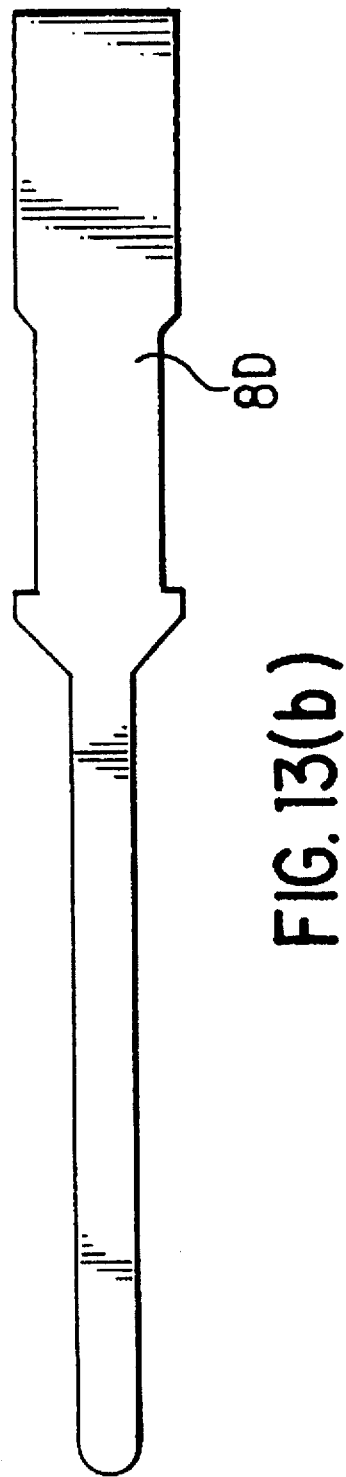
Figure 14:
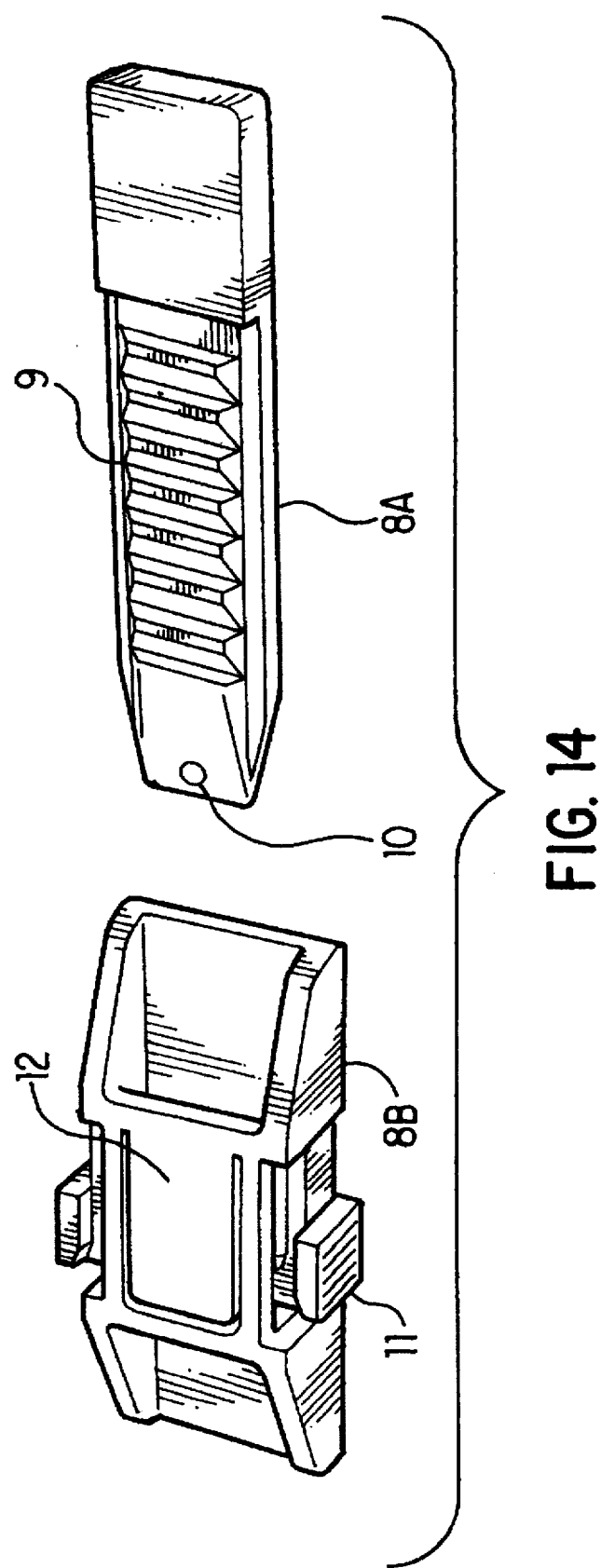
FIG. 14 is a perspective view of a slide-type one-touch strap clasp used in the invention.

FIG. 9 is a perspective view of a one-touch strap of a fourth embodiment of the invention, and FIG. 10 is a perspective view of the one-touch strap directly attached to a goggle. FIGS. 13(a) and 13(b) are plan views of rubber straps of the fourth embodiment. FIG. 14 is a perspective view of a slide-type one-touch strap clasp of the fourth embodiment.

One end of each rubber strap is attached to a main body of a goggle 1, and the other end of each rubber strap is provided with a slide stopper (slide-type strap clasp) 8 which is used to tighten or loosen the rubber strap with one touch. The slide stopper 8 is formed of a slide stopper wave-shaped insert 8A, and a slide stopper socket 8B. Rubber straps 8C, 8D are installed on the back side of the slide stopper wave-shaped insert 8A and the socket 8B. At an end of the slide stopper wave-shaped insert 8A, there is a protruding separation preventer 10, which prevents the slide stopper wave-shaped insert 8A and the slide stopper socket 8B from separating and falling-off when the wave-shaped insert is loosened within the socket.

The slide stopper wave-shaped insert 8A has a wave-shaped part 9 on the front side, which is on the opposite side of the rubber strap 8C. The wave-shaped part 9 extends from near the position of the rubber strap 8C to near the slide stopper's separation preventer 10. The rubber strap 8D is installed on the back side of the slide stopper socket 8B, which has a holding flap 12 for the wave-shaped part 9 and slide stopper socket's buttons 11.

The present invention has the above-mentioned structure, and in order to use this, one end of each of the rubber straps 8C and 8D is attached directly to the right or left strap attachment hole 1A of the main body 1 of the goggle, or indirectly to the main body by using the strap attachment fixture 7. The other end of each of the rubber straps 8C and 8D is fixed to each of the slide stopper part 8A and the socket 8B. The slide stopper part 8A has many wave-shaped grooves whose slope is made for easy and smooth insertion of the slide stopper part 8A into the socket 8B. The socket 8B has the holding flap 12 with the hook, which engages the wave-shaped part 9 to prevent the slide stopper part 8A from being pulled out. However, the slide stopper part 8A can be moved in the pulling-out direction by pressing the buttons 11 of the socket 8B, which push the hook of the holding flap 12 to disengage the wave-shaped grooves. The slide stopper part 8A can be loosened for a desired length by releasing the wave-shaped grooves.

Although the slide stopper 8 is placed on the back of the head while the goggle is being used, handling of the slide stopper is simple, because insertion of the slide stopper part 8A into the socket 8B is easy and releasing of the slide stopper part 8A is also easy by pressing the buttons 11 on both sides of the socket 8B with the fingers. Therefore, the great advantage of this slide-type one-touch strap is a fine adjustment of tension by adjusting the stroke of the wave-shaped part to apply proper tension to the rubber straps. Namely, in water, proper tension is applied to prevent water from entering into the goggle and to prevent the goggle from slipping down, and on the ground, uncomfortable pressure on a user's face and eye region is eliminated by releasing the tension to provide the user similar to wearing the regular eyeglasses. Even if the strap's tension is reduced, the slide stopper part 8A does not easily separate from the socket 8B due to the separation preventer 10 on the slide stopper wave-shaped insert. The slide stopper insert 8A, however, can be pulled out from the socket 8B while pressing the buttons 11.

The proper length and width of the rubber straps in the fourth embodiment is about 20 to 30 cm and 7 to 30 mm, respectively. The slide stopper socket 8B of the slide stopper 8 in FIG. 14 has a space enough for the slide stopper wave-shaped insert 8A to be smoothly inserted and narrow enough for the slide stopper socket's buttons 11 to hold the insert 8A in the socket 8B. The proper length of the wave-shaped part of the slide stopper wave-shaped insert 8A is about 70 to 100 mm. The proper length of the slide stopper socket 8B is about 35 to 55 mm and should not be too long to be in style or too short to prevent water from entering into or the slipping down of the goggle. The material for the slide stopper 8 must not hurt skin or hands of a User softened in water, and it is better to ensure safety and enable simple handling.

The rubber straps 8C and 8D in FIGS. 13(a) and 13(b) are designed to match the width and length of the attaching part (e.g. an inlay attachment) of the slide stopper wave-shaped insert 8A and the slide stopper socket 8B or to lengthen the wider part of the straps 8C and 8D, and are attached to 8A and 8B, respectively. The strap loop 6 in FIG. 12(c) can be installed to enter an extended part of the slide stopper wave-shaped insert 8A thereinto, which projects when the slide stopper is set so as to apply proper tension. Thus, this part is placed along the shape of the head to reduce resistance to water flow while the wearer is swimming. A reticulate pattern may be made on the back side of the rubber straps to increase the function for slip prevention and stability of the fit of the goggle.

To fix the rubber straps, waterproof adhesives must be used. As for the adhesion of the rubber straps 8C and 8D to the slide stopper 8, not only the adhesion with adhesives but also with any fastening methods including inlay attachment can be used to satisfy required conditions, such as water resistance and adhesion strength. Monolithic molding (integral molding) of these parts may be also applicable by using hard rubber and other resin-based materials.

Natural rubber, synthetic rubber, and silicone rubber are used for the rubber strap, but other materials may also be applicable. Color of the rubber strap is selected to match the main body of the goggle or the rubber straps may have any colors that can be considered fashionable.

The proper thickness of rubber straps is about 0.5 to 2.5 mm because of the structure of the strap attachment hole of the main body of the goggle and the tension and strength of the rubber straps. It is possible to form for slip prevention linear pattern protrusions (for example, at intervals of 3 mm to 1 cm) or reticulate pattern on the surface of the rubber strap in the adjustable range.

Although most swimming goggles have functions at strap attachment holes to adjust the length of the rubber straps and also to fix the rubber straps, some strap attachment holes are not adequate for directly attaching the straps. Therefore, as a fifth embodiment, the strap attachment fixture 7 in FIG. 12(d) is prepared separately to be installed at the position 3C in FIGS. 3 and 7. The hook of the strap attachment fixture 7 is connected to the strap attachment hole 1A.

As mentioned above, in the invention, the goggle is stabilized; the length of the strap can be adjusted; and the structure is simple, and fits around the back of the head well with great fashionability. One-touch straps for the swimming goggle have sliding functions in their fastening parts which enable the tension of the straps to be delicately adjusted. These one-touch straps, which can be attached easily to any swimming goggles, can be used easily by eliminating the feeling of pressure while the goggles are being used outside water. Eyeglass users need not carry a pair of regular glasses in addition to the goggle when they swim or rest by the side of a swimming pool or at a beach. They can avoid annoyance of repeatedly exchanging goggles with eyeglasses and all the danger and troubles associated with their poor eyesight. Thus, this invention demonstrates its great effectiveness.

What is claimed is:

1. One touch tension adjustment device for a goggle with attachment holes, comprising:

an expandable strap adapted to be attached to the goggle and having a holding section first and second end portions, said first end portion having a sliding area, the first end portion having an area overlapping with the holding section, a connecting device attached to an end of the first end portion to fix the end of the first end portion to the strap to increase an overlapping area of the strap in a tension apply condition for the strap, and a tension adjustment stopper fixed to the strap at an end of the sliding area so that in the tension apply condition for the strap, when the connecting device is released, the overlapping area of the strap is reduced to reduce tension of the tension apply condition, and the tension adjustment stopper moves close to the goggle.

2. One touch tension adjustment device according to claim 1, wherein said connecting device includes a socket and an insert, one of the socket and insert being fixed to the first end.

3. One touch tension adjustment device according to claim 2, wherein the other of the socket and the insert is fixed to the second end portion, said second end portion having an additional sliding area, said adjustment device further including an additional tension adjustment stopper fixed to the additional sliding area.

4. One touch tension adjustment device according to claim 3, further comprising at least one length adjustment piece situated at at least one of the first and second end portions to adjust the position of the connecting device at said at least one of the first and second end portions, and strap loops loosely attached to the strap.

5. One touch tension adjustment device according to claim 3, further comprising two end straps, and connection rings, one end of each of the end straps being fixed to one of the attachment holes of the goggle and the other end of each of the end straps being fixed to the connection ring, said sliding areas of the first and second end portions slidably engaging the connection rings.

6. One touch tension adjustment device according to claim 2, wherein the other end of the socket and the insert is fixed to a center portion of the strap, said adjustment device further including a second connecting device formed of a socket, an insert and an additional tension adjustment stopper fixed to an additional sliding area of the second end portion, one of the socket and the insert of the second connecting device being fixed to an end of the second end portion, and the other of the socket and the insert of the second connecting device being fixed to the center portion of the strap.

7. One touch tension adjustment device according to claim 6, further comprising at least one length adjustment piece situated at at least one of the first and second end portions to adjust position of the connecting device at said at least one of the first and second end portions.

* * * * *